United States Patent [19]

Callahan et al.

[11] Patent Number: 5,186,941
[45] Date of Patent: Feb. 16, 1993

[54] VESICLE FORMULATION FOR THE CONTROLLED RELEASE OF THERAPEUTIC AGENTS

[75] Inventors: Richard A. Callahan, S. Pasadena; George W. Tin, Arcadia, both of Calif.

[73] Assignee: Vestar, Inc., San Dimas, Calif.

[21] Appl. No.: 794,777

[22] Filed: Nov. 18, 1991

Related U.S. Application Data

[63] Continuation of Ser. No. 136,455, Dec. 21, 1987, abandoned, which is a continuation of Ser. No. 904,849, Sep. 5, 1986, abandoned, which is a continuation of Ser. No. 606,450, Apr. 30, 1984, abandoned, which is a continuation-in-part of Ser. No. 492,297, May 6, 1983, abandoned.

[51] Int. Cl.$^5$ .................... A61K 9/127; A61K 9/133
[52] U.S. Cl. .................... 424/450; 264/4.1; 264/4.3; 424/1.1; 428/402.2; 514/823; 514/885; 514/963
[58] Field of Search .................... 264/4.1, 4.3; 424/1.1, 424/450; 428/402.2; 436/829; 514/823, 963

[56] References Cited

U.S. PATENT DOCUMENTS

| | | | |
|---|---|---|---|
| 4,089,801 | 5/1978 | Schneider | 264/4.1 |
| 4,186,183 | 1/1980 | Steck et al. | 264/4.1 X |
| 4,224,179 | 9/1980 | Schneider et al. | 436/4.3 |
| 4,229,360 | 10/1980 | Schneider et al. | 424/450 X |
| 4,342,826 | 8/1982 | Cole | 436/829 X |
| 4,411,894 | 1/1981 | Shrank et al. | 514/78 X |
| 5,094,854 | 3/1992 | Ogawa et al. | 428/402.2 X |

FOREIGN PATENT DOCUMENTS

| | | |
|---|---|---|
| 0021337 | 1/1981 | European Pat. Off. . |
| 0072234 | 2/1983 | European Pat. Off. . |
| 55-122095 | 9/1980 | Japan . |
| 0046921 | 3/1982 | Japan ..................... 424/450 |

OTHER PUBLICATIONS

R. Bittman, et al., "Osmotic Behavior of Liposomes of Phosphatidylcholine and Phosphatidylsulfocholine as a Function of Lipid Concentration", 28(4) *Chem. Phys. Lipids* pp. 323-335 (1981).

Abra, R. M. and Hunt, C. A., 666 Biochimica et Biophysica Acta, pp. 493-530 (1981).

Allen, J. M., and Cleland, L. G., 597 Biochimica et Biophysica Acta, pp. 418-526 (1980).

Allen and Everest, 226 The Journal of Pharmacology and Experimental Therapeutics, No. 2, pp. 539-544.

Osol et al., The United States Dispensatory, 27th Edition, J. B. Lippincott Co., Philadelphia, Toronto (1973), pp. 950-951.

Arakawa, E., 23 Chemical and Pharmaceutical Bulletin of Japan, pp. 2218-2222 (1975).

Bangham, 1 Chemistry and Physics of Lipids, pp. 245-246 (1967).

Burdgaard, H., editor, Alfred Benzoin Symposium #17, Optimization of Drug Delivery, p. 400 (Copenhagen 1982).

Juliano, R. L., 56 Canadian Journal of Physiology and Pharmacology, No. 5, pp. 683-690 (1978).

Kimelberg, 448 Biochimica et Biophysica Acta, pp. 531-550 (1976).

*Primary Examiner*—Richard D. Lovering
*Attorney, Agent, or Firm*—Lyon & Lyon

[57] ABSTRACT

Disclosed herein are vesicle compositions for controlled sustained release of an encapsulated therapeutic agent after parenteral administration. By adjusting the osmolarity between the suspending solution and the solution within the vesicles by adjusting the concentration of the suspending solution, the rate of release of the therapeutic agent after parenteral administration can be varied. The compositions can be effectively administered by intramuscular, subcutaneous injection or other means.

9 Claims, 5 Drawing Sheets

VESICLE FORMULATION FOR THE CONTROLLED RELEASE OF THERAPEUTIC AGENTS

This application is a continuation of application Ser. No. 07/136,455 filed Dec. 21, 1987 (now abandoned), which was a continuation of application Ser. No. 06/904,849 filed Sep. 5, 1986 (now abandoned), which was a continuation of application Ser. No. 06/606,450 filed Apr. 30, 1984 (now abandoned), which was a continuation-in-part of application Ser. No;. 06/492,297 filed May 6, 1983 (now abandoned).

FIELD OF THE INVENTION

The present invention relates to formulations for the controlled release in vivo of therapeutic agents. In another aspect, it relates to vesicles and, particularly, to phospholipid vesicles.

DESCRIPTION OF PRIOR ART

Numerous conditions in both man and lower animals are responsive to drugs or other therapeutic agents administered in vivo. To be useful, these agents must be administered at a dosage level which is high enough to cause the desired effect, and that dosage level must be maintained for a sufficient period of time to achieve that effect. Many such therapeutic agents are routinely administered by intra-muscular injection at dosage levels calculated to produce a concentration of the agent in the circulatory system which is effective. Thereafter, injections are repeated as necessary to maintain the therapeutically effective level.

It is often the case that the therapeutically effective level of the agent in circulation is maintained only a short time after injection because of breakdown of the agent by the host's defensive mechanisms against foreign substances. Moreover, the agent itself may have intolerable side effects, even lethal ones, if administered in amounts which substantially exceed the therapeutically useful level. Therefore, prolonging the effective concentration of the agent in the body by increasing the dosage is always limited by the amount of toxicity. Even in cases where toxicity is low, the size of an injection can be limited by the size of the bolus which can be administered safely.

In view of such problems, efforts have been made to develop delivery systems for therapeutic agents which may be administered in vivo and which, after administration, gradually release the agent into its environment in order to prolong the interval over which the effective concentration of the agent is maintained in that environment. In this way, the interval between administrations of the agent can be increased and, in some instances, the need for further administration can be eliminated.

One such approach to obtaining prolonged or sustained release has been to encapsulate the therapeutic agent in a "vesicle". As used herein, the term vesicle refers to a micellular particle which is usually spherical in form and which is frequently obtained from a lipid which forms a bilayered membrane and is referred to as a "liposome". Methods for making such vesicles are well known in the art. Typically, they are prepared from a phospholipid such as distearoyl phosphatidylcholine or lecithin, and may include other materials such as positively or negatively charged compounds. Vesicles made from phospholipids are commonly referred to simply as "phospholipid vesicles". Depending on the techniques for its preparation, a vesicle may form as a simple bilayered shell (a unilamellar vesicle) or it may form in multiple layers (multilamellar vesicle).

After administration, typically as a suspension in physiological saline, the vesicles gradually release the encapsulated therapeutic agent which then displays its expected effect. However, prior to its release, the agent exhibits no pharmacokinetic properties and is protected by the vesicle from metabolic degradation or other attack by the host's defense mechanisms against foreign substances. Accordingly, the agent can be safely administered in an encapsulated form in dosages which are high enough that, if directly given the host, could result in severe side effects or even death.

The time interval over which an effective concentration of the therapeutic agent is maintained after administration as a vesicle encapsulant is generally thought to be a function of the rate at which it is released from the vesicle and the rate at which it is absorbed from the point of administration after release. Since the former may vary with vesicle structure and the latter by reason of the properties of the agent, the interval over which the useful concentration of an agent in circulation is maintained can vary widely. Generally, the rate of release from the vesicle is thought to be controlling for most compounds and sustained release of encapsulated drugs over a period of 6-8 hours is a common observation. See F. J. T. Fields, (1981), *Liposomes: From Physical Structure to Therapeutic Applications; Research Monographs in Cell and Tissue Physiology*, Vol. 7, C. G. Knight, ed., Elsevier/ North Holland, N.Y., p. 51ff and R. W. Stevenson et al, *Diabetologia*, 19, 217 (1980). However, intramuscular injections in mice of vesicle encapsulated interferon resulted in localized levels of interferon which, after three days, were equivalent to levels observed over 2-4 hours after injection of free interferon. D. A. Eppstein et al, J. Virol., 41, 575. This longer time of sustained release likely reflects the lower mobility of this biomacromolecule from the injection site.

Notwithstanding the advance in sustained release which has been achieved using vesicles as encapsulants, further improvements in sustained release compositions are desirable to increase still further the interval between administrations of the therapeutic agents. Even a 6-8 hour period of sustained release makes out-patient treatment difficult, if not impossible, and longer intervals would reduce the workload of hospital or other medical personnel, not to mention reducing the patient's discomfort. Furthermore, although by vesicle encapsulation the period over which an effective concentration of therapeutic agents could be maintained is extended, no effective means to control the rate of release results from encapsulation itself. Accordingly, there remains as yet unmet, a desire for sustained release formulations of therapeutic agents which extend even further the interval over which an effective concentration of the agent is maintained.

SUMMARY OF THE INVENTION

According to the present invention, a process and a composition are provided for controlling the rate at which a therapeutic encapsulated in a vesicle is released from the vesicle after in vivo administration. This is achieved by suspending the vesicles, which encapsulate a solution of the therapeutic agent, in a solution containing sufficient solute that its osmolarity, relative to that of the solution within the vesicles, is at least substantially isotonic, that is, at least approximately 25% of the osmolarity inside the vesicles. The suspension is then administered parenterally, for example by subcutaneous or intramuscular injection.

The rate of release of the therapeutic agent from the vesicles after administration is a function of the initial osmotic pressure. Thus, as the osmolarity of the suspending solution becomes less hypotonic, relative to the solution within the vesicles, the rate of release of the therapeutic agent is slowed. Slowest releases are obtained when the suspending solution approaches an isotonic, or even hypertonic, relationship with respect to the solution within the vesicles. The compositions of the present invention exhibit a longer interval over which the sustained release of the agent is maintained compared to agents encapsulated in vesicles and administered as suspensions in physiological saline as described in the prior art.

Accordingly, an object of the invention is to improve the delivery of therapeutic agents.

Another object is to improve the delivery of therapeutic agents in sustained release formulations.

DETAILED DESCRIPTION

As noted above, the present invention provides a method for controlling the rate of release in vivo of a therapeutic agent from a vesicle encapsulant by adjusting the osmotic pressure between the solution of therapeutic agent within the vesicle and the solution in which the vesicles are suspended for parenteral administration.

In another aspect, the present invention is directed to a composition comprising a solution of a therapeutically active agent encapsulated in vesicles, the vesicles being suspended in a solution which contains sufficient solute that its osmolarity at least approaches a substantially isotonic relationship with the solution in the vesicles. When such vesicles are parenterally administered to a host, for example, intramuscularly, the interval over which sustained release is maintained is substantially increased.

Although we do not wish to be bound by any particular theory, the increase in the interval of sustained release obtained as the osmolarity of the suspending solution is made less hypotonic, relative to the solution within the vesicles, may result from the fact that, so long as the concentration of solute in the suspending solution is such that the solution is not hypotonic, that is the osmolarity approaches at least a substantially isotonic relationship with the solution within the vesicles, the osmotic pressure is not great enough to cause the solvent of the suspending solution to migrate into the vesicles which would increase the hydraulic pressure within the vesicles and cause them to break down or release part of their contents. After administration, however, the concentration of liquid medium around the vesicles gradually becomes more hypotonic with respect to the solution within the vesicles, for example, by absorption of the solute from the suspending solution. As this occurs, the osmotic pressure between the vesicles and the hypotonic liquid medium causes liquid to migrate into the vesicles, causing release of the therapeutic agent. By contrast, the prior art practice of administering the therapeutic agent in vesicles suspended in physiological saline which is already hypotonic to the vesicles results in a much more rapid release of the vesicle contents. Accordingly, the therapeutic agent is also more rapidly released. By adjusting the osmolarity between the solution of therapeutic agent and the suspending solution, however, the rate of release can be varied giving a degree of control over this rate not hitherto attained.

In the practice of the present invention, the therapeutic agent is dissolved in a suitable solvent, for example, physiological saline, usually at or near the saturation point in the case of agents of limited solubility, and encapsulated in a suitable vesicle. Techniques to do this are well known in the art and need not be described in detail here. Presently preferred for use in the invention are multilamellar phospholipid vesicles although unilamellar vesicles and vesicles of other than phospholipid can be used, the basic essential criterion being that the material of the vesicles be tolerable by the host in the amounts to be administered.

The solution used for suspending the vesicles is preferably physiological saline (~0.15M NaCl) to which has been added a second solute to adjust the concentration of this solution to a level that gives the desired rate of release. This concentration will be adjusted so that the osmoloarity of the suspending solution is substantially isotonic with the solution within the vesicles, that is, the suspending solution contains sufficient solute to provide an osmolarity that is at least approximately 25%, preferably at least 40 to 50% of the osmolarity of the solution within the vesicles. The usually desired result of the invention, i.e., lengthening the interval of sustained release, can be achieved if the osmolarity of the suspending solution is within the range from substantially isotonic to hypertonic with respect to the vesicles, with it being especially desirable for the suspending solution to be at least about 75% to about 90% of being isotonic. Since solute is thus added to the suspending solution, it will be clear that the suspending solution will have an osmolarity greater than that of physiological saline.

Suitable for use as solutes in the suspending agents are any solutes which are well tolerated by the host. Among these may be mentioned the sugars such as dextrose and the hexoses such as glucose and polypeptides which do not exhibit significant biological effects. Presently preferred is glucose as it is readily obtained as a sterile substance for administration to humans and is readily absorbed by the body.

Any of a wide variety of therapeutic agents may be used as part of the invention. Among these may be mentioned antibiotics, metabolic regulators, immune modulators, toxin antidotes, etc. For example, the invention is well suited for the controlled release of antidotes to cholinesterase inhibitors.

In order to demonstrate the advantages of the present invention, there follows a description of experiments carried out with vesicle encapsulated 2-pralidoxime chloride (2-PAMCl), an agent which is a well known and thoroughly studied antidote to toxic organophosphates which inhibit cholinesterase. Persons exposed to such intoxicants in lethal amounts suffer cardiac insufficiency or respiratory paralysis which results in death. Agents such as 2-PAMCl reactivate cholinesterase if administered in a timely fashion. However, dosages of 2-PAMCl high enough to maintain the therapeutic level for a long period of time cannot be administered because undesirable side effects, even death, can result.

EXPERIMENTAL RESULTS

A. Materials

L-α-distearoyl phosphatidylcholine (DSPC), L-α-dipalmitoyl phosphatidylcholine (DPPC) from Calbiochem, and cholesterol (Chol), stearylamine (SA), and dicetylphosphate (DCP) from Sigma Chemical Company were used without further purification to prepare vesicles. 2-Pyridinealdoxime (2-PAM), pralidoxime chloride (2-PAMCl) and Iodomethane were purchased from Aldrich Chemical Company and AG 1×8 ion exchange resin was from BioRad Laboratories (Richmond, Calif.). Ultrapure $InCl_3$ was purchased from Ventron Corporation (Danvers, Mass.). [$^3$H]-cholesterol oleate (specific activity: 52 Ci/mole) and [$^{14}$C]-Iodomethane (specific activity: 10 Ci/mole) were purchased from New England Nuclear. Carrier-free $^{111}InCl_3$ was purchased from Medi-Physics (Glendale, Calif.) and purified according to the method of Hwang and Mauk, *Proc. Natl. Acad. Sci. USA*, 74, 4991 (1977). The ionophore A23187 was from Eli Lilly and Co. Sprague-Dawley rats in the range of 200-250 g were purchased from Charles River Laboratories and kept in an AAALAC approved laboratory for one week before use in experiments.

B. Methods

Preparation of Vesicles

Small unilamellar vesicles (SUV's) were prepared by probe sonication of the lipid mixture in phosphate buffered saline (PBS) containing either nitrilotriacetic acid (NTA) or 2-PAMCl. See Mauk et al, *Anal. Biochem.*, 94, 302, 307 (1979). A trace amount of [$^3$H]cholesterol oleate was included in the lipid mixture as a marker for the lipid phase. Following sonication, annealing, and low speed centrifugation, the NTA external to the vesicle was removed by passage of the preparation over a Sephadex G-50 column, equilibrated with PBS.

Large unilamellar vesicles (LUV's) were prepared by the reverse phase evaporation (REV) method described by Szoka and Papahadjopoulos, *Proc. Natl. Acad. Sci. USA*, 75, 4194 (1978). REV vesicles are formed when an aqueous buffer containing the material to be encapsulated is introduced into a mixture of phospholipid and organic solvent, and the organic solvent is subsequently removed by evaporation under reduced pressure. The REV vesicles are then passed through a gel permeation column to remove the solvent residue and the unencapsulated drug.

Multilamellar vesicles (MLV's) were prepared by stirring the dry lipid film with the material to be encapsulated. Free unencapsulated materials can be separated from MLV encapsulated material by centrifugation at 12,000×g. In our preparation of MLV's for in vivo injection, 40 mg of DSPC:Chol (2:1 molar ratio) (or other compositions as indicated) were stirred for ½ hour in a round bottom flask with 1-2 ml of PBA containing 0.5M 2-PAMCl, or 3M 2-PAMCl as indicated.

Synthesis of [$^{14}$C] 2-PAMCl

Radiolabeled 2-PAMCl for use in the studies could not be obtained from any source. Therefore, the radiolabeled drug was synthesized. [$^{14}$C] labeled 2-Pralidoxime Iodide (2-PAMI) was first synthesized by refluxing 2-pyridine aldoxime (2-PAM) with [$^{14}$C]-methyl iodide in nitrobenzene for three hours at 75°-80° C. The reaction was then stopped, and the yellow precipitate of 2-PAMI was filtered and recrystallized from methanol. These yellow crystals of 2-PAMI were then dissolved in a minimal amount of water and passed through an anionic exchange column (BioRad AG 1×8). The chloride salt of 2-PAM was isolated by drying the solution with a rotary evaporator followed by recrystallization from ethanol. Approximately 1.5 gm of pure [$^{14}$C]labeled 2-PAMCl was obtained with specific activity of 25 μCi/mole. The chemical identity of this material was confirmed by (1) the melting point of the compound which was found to be 232°-234° C. (literature value 235° C.) and (2) the characteristic absorption of an acidic solution of 2-PAMCl at approximately 295, 245, and 210 nm; and (3) co-migration during thin layer chromatography of the $^{14}$C labeled compound with 99% pure 2-PAMCl.

In Vitro Vesicle Studies

The chemical structure of vesicles was altered by varying the length of their phosphatidylcholine carbon chain, cholesterol content, and surface charge. The stability of the vesicle formulations in vitro was studied by gamma-ray perturbed angular correlation spectroscopy (PAC) as described by Hwang and Mauk, *Proc. Natl. Acad. Sci. USA*, 74, 4991 (1977). Prior to PAC measurements the vesicles were loaded with $^{111}InCl_3$. Typically 1.0 mg of vesicles with the ionophore A23187 incorporated within the bilayer was incubated with $^{111}InCl_3$ at 80° C. for 45 minutes. During incubation, the $^{111}In$ passed through the ionophore and complexed with NTA inside the vesicles. The remaining $^{111}In$ outside the vesicle was subsequently complexed to EDTA and separated from the loaded vesicles by chromatographing the mixture on a Sephadex G-50 column equilibrated with PBS. The vesicles, now loaded with $^{111}In$-NTA, were then suspended in a 1:1 solution of physiological saline and rat plasma. Gamma-ray PAC specstrocpy was then used to monitor the structural integrity of vesicles by measuring the tumbling rate of $^{111}In^{+3}$.

$^{111}In^{+3}$ chelated to nitrilotriacetic acid exhibits a fast tumbling rate. However, upon disruption of the vesicle, the released $^{111}In^{+3}$ rapidly binds to macromolecules in the surrounding medium and exhibits a markedly decreased tumbling rate. Repeated PAC measurements of each vesicle formulation were used to estimate vesicle stability based on the time course for the release of $^{111}In$.

Similarly, identical vesicle formulations loaded with [$^{14}$C]-2-PAMCl were used to measure the release rate of 2-PAMCl. Aliquots were periodically withdrawn from each preparation and free 2-PAMCl separated from the microencapsulated drug by gel filtration chromatography as described by Huang, *Biochem*, 8, 344 (1969). The amount of [$^{14}$C]-2-PAMCl remaining within the vesicles was measured by liquid scintillation counting.

In Vivo Vesicle Studies

The rate of release of [$^{14}$C]-2-PAMCl from the various vesicle formulations was measured in vivo using male Sprague-Dawley rats obtained from Charles River Inc. Dosages ranging from 5–240 mg/kg body weight (BW) of free and encapsulated [$^{14}$C]-2-PAMCl were injected into the thigh muscle. Individual injection volumes never exceeded 0.15 ml. At scheduled times after injection, the rats were either sacrificed or bled through the eye orbit. Radiolabeled 2-PAMCl was measured in blood and plasma by liquid scintillation counting using the New England Nuclear procedure for counting labeled biological material. See *L.S.C. Note,* #44, New England Nuclear Applications Laboratory, Boston, Mass.

C. Results

In Vitro Vesicle Stability

Figure 1:
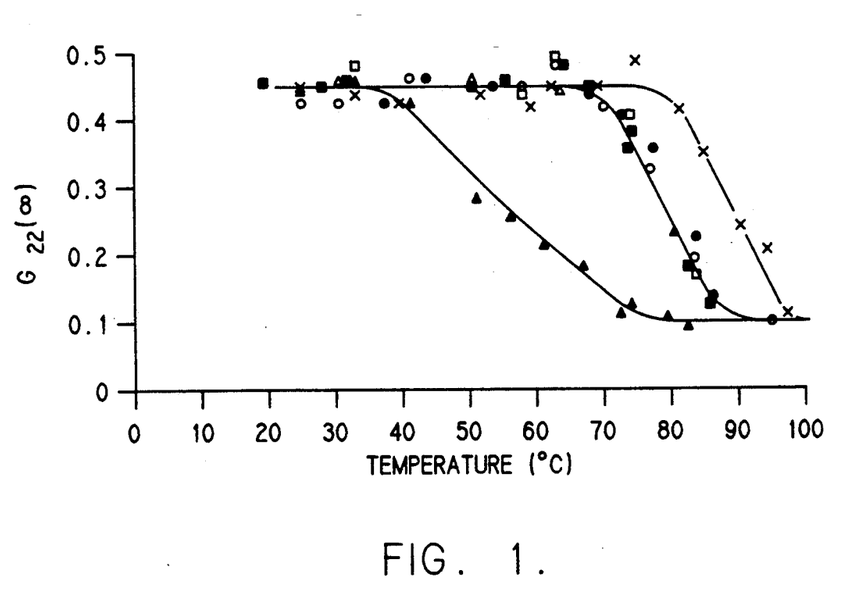
FIG. 1 illustrates the effect of temperature on the stability of vesicle formulations.

As indicated in the previous section, the rate of $^{111}$In release from vesicles in the presence of plasma can be monitored by PAC spectroscopy. FIG. 1 shows the percent $^{111}$In remaining encapsulated with seven vesicle formulations varying in cholesterol concentration, carbon chain length, and surface charge. With the exception of the negatively-charged DCP vesicle, all vesicle formulations with 33 mole percent or more cholesterol exhibited the same transition temperature as monitored by $^{111}$In release. The DCP formulation produced vesicles with a transition temperature ($^{111}$In release) approximately 10° C. higher than other vesicle formulations containing the same amount of cholesterol.

In Vivo Results

Figure 6A:
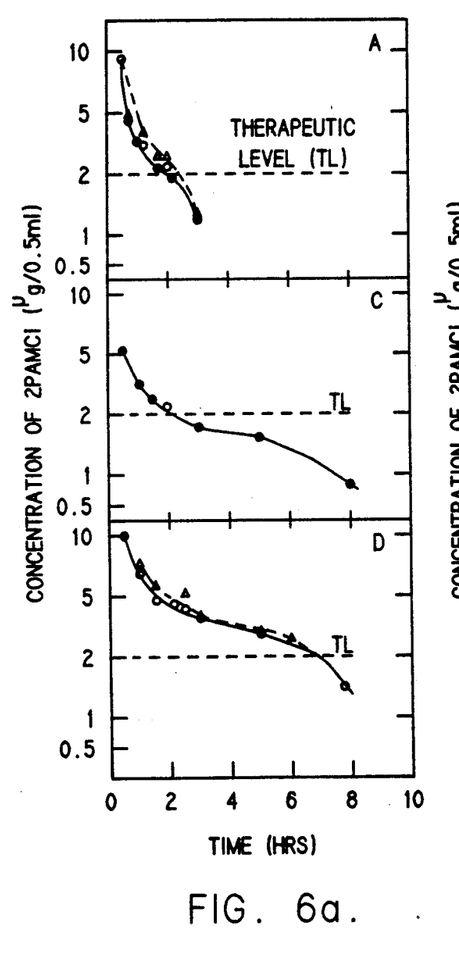
FIG. 6a illustrate the effect of suspending 2-PAMCl loaded vesicles in a solution substantially isotonic to the vesicles over a time period of 10 hours.

In the following results, the data are presented as the concentration of 2-PAMCl as a function of time for various vesicle formulations. The time dependence for a standard injection of free 2-PAM Cl shows that the blood concentration drops below therapeutic level (TL) in 2–3 hrs (FIG. 6a–A). As will be shown, all vesicle formulations with encapsulated 2-PAMCl exhibited extended blood levels. Therapeutic levels of drug were maintained typically 6–8 hrs for those formulations having only buffered saline as the suspending medium. Vesicles suspended in a high osmolar medium showed dramatically longer therapeutic levels.

The Effect of Altering the Chemical Composition of the Vesicle Membrane

Figure 2:
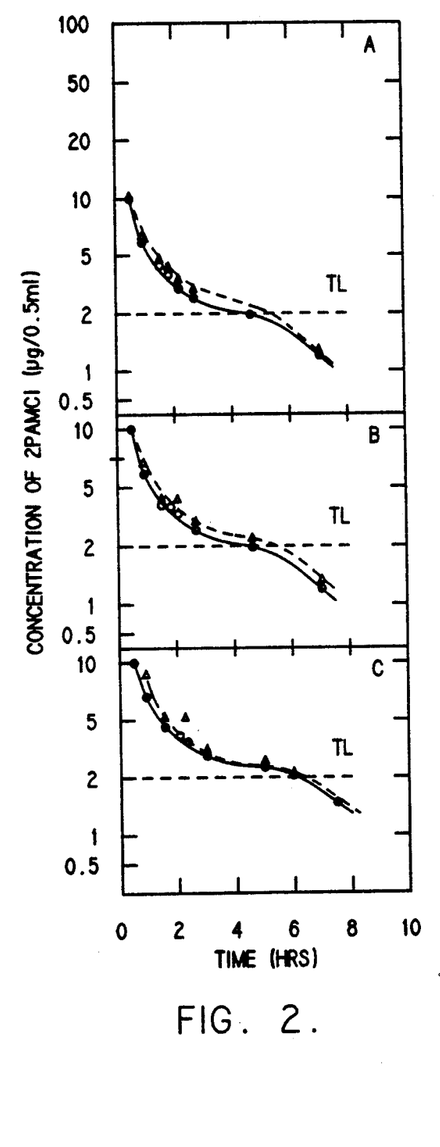
FIG. 2 illustrates the effect of vesicle membrane fluidity on sustained release of 2-PAMCl.
Figure 3:
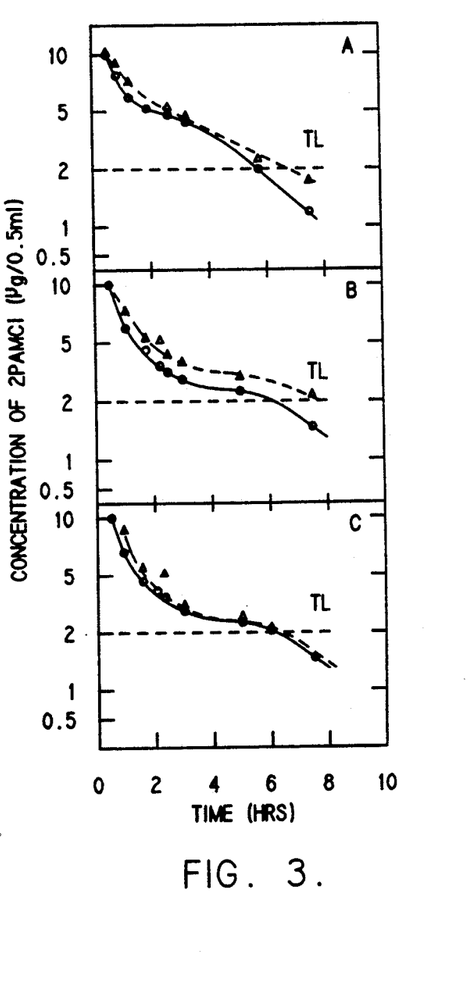
FIG. 3 demonstrates the effect of vesicle composition on sustained release of 2-PAMCl.

Altering membrane fluidity by changing lipid composition did not affect the extended release period achieved with all vesicle formulations (FIG. 2). Similarly, altering the lipid composition and charge of the vesicle membrane did not significantly alter the release period either. (FIG. 3).

Figure 4:
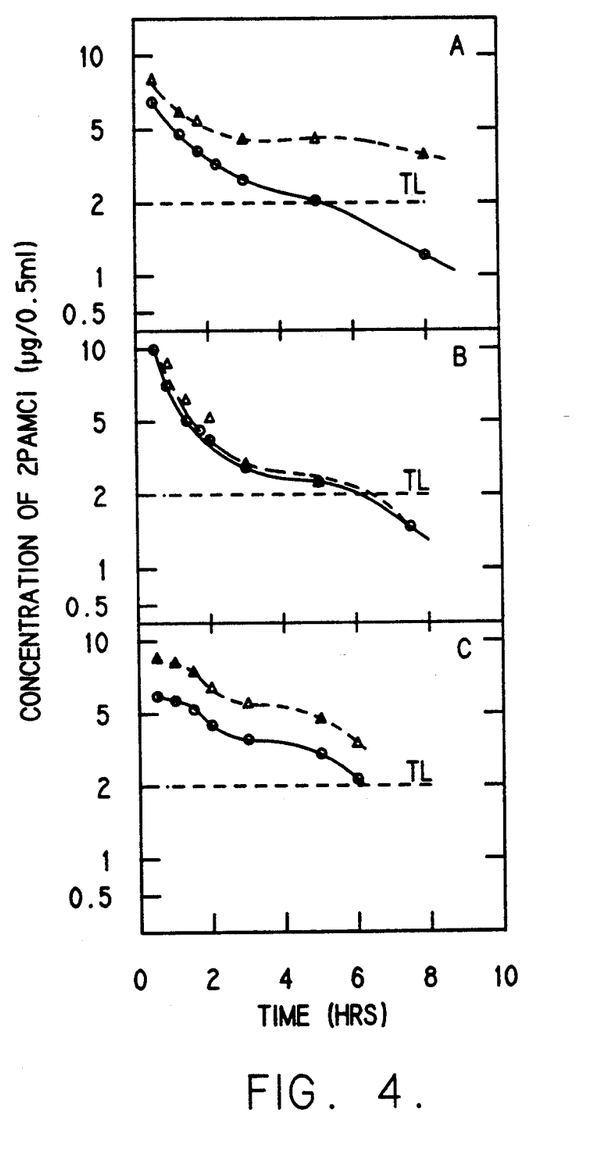
FIG. 4 illustrates the effect of cholesterol content of phospholipid vesicles on sustained release of 2-PAMCl.

Among the vesicle composition and charge variables studied, the only factor affecting the release rate for 2-PAMCl was cholesterol content. Increasing the cholesterol content of vesicle membranes from 12.5–50.0 mole percent appeared to slightly lengthen the time therapeutic levels of 2-PAMCl remained in circulation (FIG. 4).

The Effects of Altering the Physical Structure of Vesicles

Figure 5:
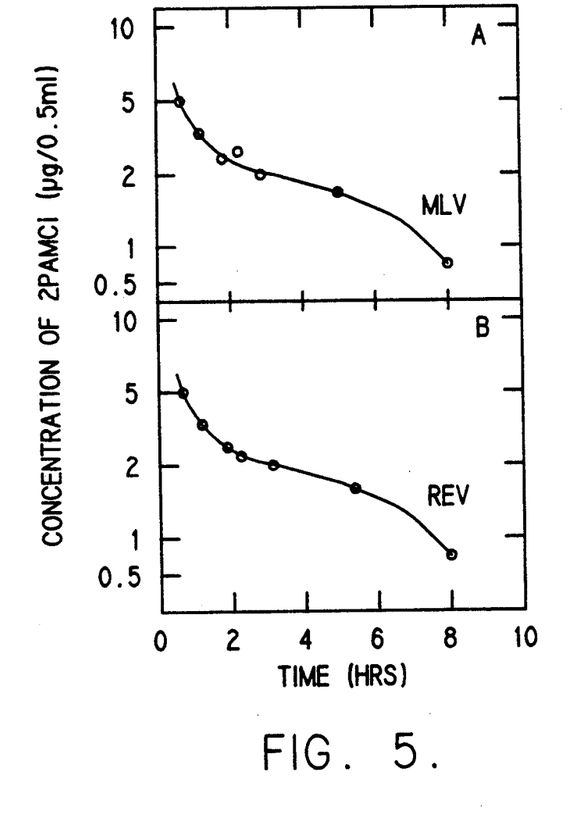
FIG. 5 illustrates the effect of vesicle physical structure on sustained release of 2-PAMCl.

The effect of vesicle structure on the extended release of 2-PAMCl was examined using multilamellar vesicles (MLV's) and large unilamellar vesicles (LUV-s) prepared by reverse phase evaporation (REV) vesicles. As shown in FIG. 5, DSPC: Cholesterol vesicles possessing the two distinct structures exhibited essentially identical 2-PAMCl release properties. Consequently MLV's containing 30 mole percent cholesterol were used in the high osmolarity studies as described below.

The Effects of Altering Encapsulation Volume and Using High Osmolar Suspending Solution The above data show that there are comparatively small changes in the time dependency of 2-PAMCl blood-levels for the formulations tested. The results indicate that simple manipulation of vesicle composition and morphology are not likely to provide extended release beyond 6–8 hrs. These results are consistent with other published observations which show modest extended release times.

Presented below are results which show that blood levels of 2-PAMCl can be dramatically extended by increasing the osmolarity of the medium in which the vesicles are suspended. Also, proportionately higher concentrations of drug can be encapsulated without leakage from the vesicles.

Figure 6B:
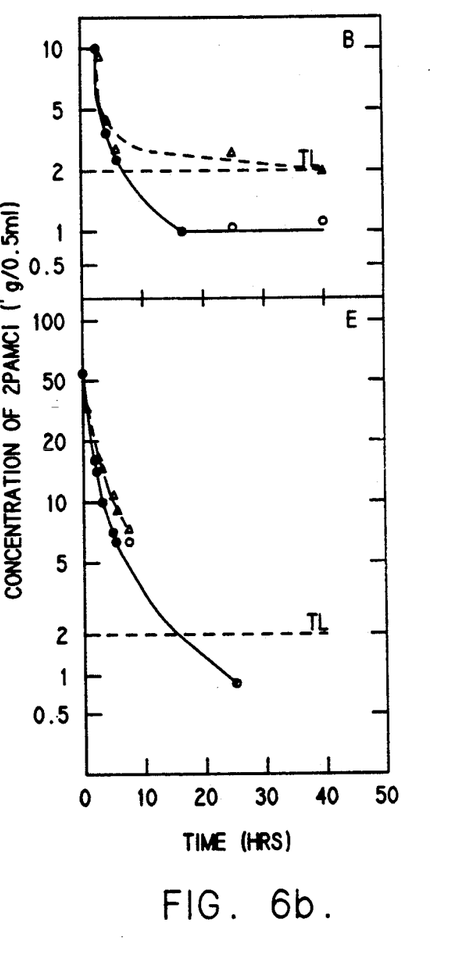
FIG. 6b illustrates the effect of suspending 2-PAMCl loaded vesicles in a solution substantially isotonic to the vesicles over a time period of 50 hours.

The most effective vesicle formulations for extending the therapeutic plasma levels (4.0 μg/ml plasma) in rats was found to be a 2:1 DSPC:Cholesterol lipid mixture, formed as MLV's and encapsulating a 3 molar solution of [$^{14}$C]-2-PAMCl which was suspended in an isomolar glucose-physiological saline solution 3M in glucose, after working to remove mother liquor. In this case, the osmolarity of the suspending medium is about 60% of the osmolarity of the encapsulated drug. Intramuscular injections (0.15 ml) of this vesicle formulation extended the therapeutic plasma drug level from 2¼ hours, obtained with the conventional saline formulation, (FIG. 6a-A), to at least 40 hours (FIG. 6b–B). Animals receiving the isomolar vesicle formulation exhibited no toxic symptoms and their blood drug levels never exceeded the 20 μg/ml level achieved by control animals receiving the standard 12 mg 2-PAMCl saline formulation (FIG. 6a–A).

The extension of therapeutic blood levels is related to the amount of drug encapsulated. All encapsulation techniques extended the maintenance of therapeutic drug levels. Doubling the encapsulating lipid material from 2.5 mg to 5.0 mg by doubling the quantity of lipid (and thereby increasing encapsulated volume of drug solution) increased the time that therapeutic levels were maintained from 2.5 to 7.0 hours (FIG. 6a–C,D). Similarly increasing the amount of drug encapsulated from a saline solution containing 60 mg of 2-PAMCl prevented all acute toxic symptoms while extending the therapeutic blood titers to 15 hours (FIG. 6d–E). All animals receiving similar 60 mg injections of 2-PAMCl unencapsulated in saline solution, or encapsulated using a technique which reduces the encapsulation efficiency died within 30 minutes after injection.

These data suggest that encapsulated drug acts as a third compartment from which its slow release lowers the peak blood levels seen when equal, unencapsulated dosages are injected. This delayed release prevents toxic blood levels from being attained and conserves drug for later therapeutic use. All encapsulation systems tested extended the time therapeutic blood levels of drug were maintained from 2.25 hours to about 6.0 hours. However, the chemical structure of the lipid membrane and the physical structure of the vesicle (whether MLV, SUV, or LUV) had little effect on extending therapeutic blood levels.

The foregoing demonstrates that suspension of vesicle formulations containing a therapeutic agent in a solution that approaches being isotonic or even hypertonic with respect to the vesicle greatly extends the interval over which sustained release occurs. It further demonstrates that dose levels of a therapeutic agent which are toxic when the agent is administered alone or in less effective sustained release formulations can be safely given using a composition of the present invention.

It will be understood by those skilled in the art that the foregoing merely illustrates the presently preferred embodiments of the invention and that modifications may be made in order to accomplish specific ends which do not depart from the spirit of the present invention which is to be limited only by the appended claims.

I claim:

1. A composition comprising a solution of a therapeutic agent encapsulated in vesicles, the vesicles being suspended in a solution containing sufficient solute selected from the group consisting of sugars and polypeptides to provide an osmolarity of the suspending solution which is hypertonic, with respect to the solution within the vesicles and which is of greater osmolarity than physiological saline, said composition being capable of controlling the release in vivo of said therapeutic agent and capable of subcutaneous and intramuscular administration to a host.

2. A composition according to claim 1 wherein said solute is a hexose.

3. A composition according to claim 1 wherein the solute is glucose.

4. A process for administration to a host of a therapeutic agent encapsulated in vesicles, comprising administering to the host a suspension of the agent in vesicles, the vesicles being suspended in a solution containing sufficient solute selected from the group consisting of sugars and polypeptides to provide an osmolarity which is at least about 25% of the osmolarity of the solution within the vesicles and which is of greater osmolarity than physiological saline to control the release in vivo of said therapeutic agent.

5. A process according to claim 4 wherein the osmolarity of the suspending solution is at least about 40 to about 50% of the osmolarity of the solution within the vesicles.

6. A process according to claim 4 wherein the osmolarity of the suspending solution is at least about 75 to about 90% of the osmolarity of the solution within the vesicles.

7. A process according to claim 4 wherein the suspending solution is hypertonic with respect to the solution within the vesicles.

8. A process according to claim 4, wherein said solute is hexose.

9. A process according to claim 4, 5, 6 or 7 wherein the solute is glucose.

* * * * *